United States Patent
Hantash

(10) Patent No.: US 9,554,746 B1
(45) Date of Patent: Jan. 31, 2017

(54) SYSTEM FOR EVALUATING SKIN TREATMENT

(71) Applicant: Escape Therapeutics, Inc.

(72) Inventor: Basil M. Hantash, Hughson, CA (US)

(73) Assignee: Escape Therapeutics, Inc., San Jose, CA (US)

( * ) Notice: Subject to any disclaimer, the term of this patent is extended or adjusted under 35 U.S.C. 154(b) by 143 days.

(21) Appl. No.: 14/255,706

(22) Filed: Apr. 17, 2014

Related U.S. Application Data

(60) Provisional application No. 61/813,594, filed on Apr. 18, 2013.

(51) Int. Cl.
| | |
|---|---|
| *G01N 33/48* | (2006.01) |
| *G01N 33/50* | (2006.01) |
| *A61B 5/00* | (2006.01) |
| *A61N 1/40* | (2006.01) |
| *G06F 19/24* | (2011.01) |
| *G06F 19/12* | (2011.01) |

(52) U.S. Cl.
CPC ............ *A61B 5/4848* (2013.01); *A61B 5/4836* (2013.01); *A61B 5/7282* (2013.01); *A61N 1/403* (2013.01); *G06F 19/12* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 2002/0127255 A1* | 9/2002 | Pillai et al. | 424/401 |
| 2009/0036545 A1* | 2/2009 | Chaudhuri | 514/733 |

OTHER PUBLICATIONS

Willey et al. Elastometry and clinical results after bipolar radiofrequency treatment of skin. Dermatol Surg, 2010, vol. 36, pp. 877-884.*
Hantash et al. Bipolar fractional radiofrequency treatment induces neoelastogenesis and neocollagenesis. Lasers in Surgery and Medicine, vol. 41, 2009, pp. 1-9.*

* cited by examiner

*Primary Examiner* — Russell S Negin
(74) *Attorney, Agent, or Firm* — Aka Chan LLP

(57) ABSTRACT

A system allows determining treatment parameters or sets of parameters applicable to electromagnetic radiation (EMR)-based device skin treatments that allow for upregulation of the sirtuin family of genes post treatment, while avoiding increasing collagen production. The system can be applied to other skin procedures, including chemical treatments, microdermabrasion treatments and others. The system includes classifying patient data into classifications of skin treatment and treatment parameters based on patient baseline levels. The system can determine effective treatment parameters for patients on an individual basis, to yield a healthy wound dealing response. In a specific implementation, the system determines the parameters of EMR and chemical based treatments that increase sirtuin gene expression post treatment, but do not induce collagen production.

19 Claims, 5 Drawing Sheets

SYSTEM FOR EVALUATING SKIN TREATMENT

CROSS-REFERENCE TO RELATED APPLICATIONS

This patent application claims the benefit of U.S. provisional application 61/813,594, filed Apr. 18, 2013, which is incorporated by reference along with all other references cited in this application.

BACKGROUND OF THE INVENTION

The present invention relates to the field of cosmetic treatment, and more specifically, to providing systems and methods to determine the treatment parameters in electromagnetic radiation device-based skin treatments which can upregulate specific genes of interest, and to evaluate other dermatological treatment systems for skin rejuvenation.

The harmful effects of ultraviolet (UV) radiation have led to the development of a wide array of treatments aimed at reversing photodamage. These include topical retinoids, chemical peels, microdermabrasion, and the use of noninvasive electromagnetic radiation (EMR) devices (e.g., lasers, light emitting diodes, intense pulsed light, and ultrasound). A minimally invasive, microneedle-based bipolar fractional radiofrequency (FRF) system for treatment of facial skin laxity and rhytides. The mechanisms underlying this reversal can involve initiation of dermal remodeling leading to removal of photoaged dermal tissue and its replacement with new collagen and elastin.

However, studies have indicated that there is not always a direct correlation between collagen denaturation and the extent of clinical improvement in skin quality. Furthermore, recent clinical data also showed that FRF treatment too resulted in overall skin textural improvement, suggesting that dermal FRF treatment also induced anti-aging effects on the epidermal layer.

There is a need to seek novel biomarkers that better correlate with clinical outcomes post-treatment with EMR-based devices. One potential target is sirtuins, a novel family of genes thought to regulate life span and improve stress resistance by controlling key cellular metabolic and signaling pathways. Sirtuin activity may be a quantitative corollary for treatment efficacy of skin rejuvenation therapies. Its short term potential role in mediating the local anti-aging effects of EMR-based device treatments remains largely unexplored.

Therefore, there is a need to develop systems, methods, and devices to determine the treatment parameters in EMR based device treatments that upregulate sirtuin expression that do not induce collagen synthesis.

BRIEF SUMMARY OF THE INVENTION

A system allows determining the distinct treatment parameters or sets of parameters applicable to all EMR-based device treatments that allow for upregulation of the sirtuin family of genes, while avoiding increasing collagen production. The system is not limited to EMR-based treatments, but is applicable to determining treatment parameters for other treatments including chemical treatments (e.g., chemical peels), microdermabrasion, and others. The system can also allow evaluating treatment efficacy and treatment selection based on an individual patient basis. The system can be used in medical and cosmetic procedures, such as skin rejuvenation therapies.

A first set of treatment parameters for a skin treatment device causes upregulation of expression of the sirtuin family of genes in the tissue post treatment. A second set of treatment parameters for the skin treatment device causes increase in collagen production in the tissue post treatment. The second set of parameters can be different from, identical to, or include components of the first set of parameters. A third set of treatment parameters for the skin treatment device causes upregulation of sirtuin expression and an increase in collagen production in the tissue post treatment. The third set of parameters can be different from, identical to, or include components of the first set of parameters or the second set of parameters. In implementations, the set of parameters includes an energy output of the device, a duration of the treatment, and a temperature setting for the tissue. The treatment parameters can be used in EMR-based treatments, chemical treatments (e.g., chemical peels), microdermabrasion treatments, and other skin treatments to cause upregulation in the expression of biomarkers in the tissue.

A method for inducing expression of a biomarker in tissue after a treatment is applied to the tissue includes inputting a first set of parameters into a treatment device. In a specific implementation, the biomarker is a sirtuin gene where the sirtuin gene expression is increased by the set of parameters. In another specific implementation, the biomarker is a collagen deposition and production value, where the collagen production is increased by the set of parameters. In yet another specific implementation, the set of parameters can cause both an increase in the expression of sirtuin and production of collagen in the tissue. The treatment parameters are input into a device of a EMR-based treatments, chemical treatments (e.g., chemical peels), microdermabrasion treatments, and other skin treatments to cause upregulation in the expression of biomarkers in the tissue.

The system includes: selecting a population sample, performing treatment, and collecting patient data for this sample; storing the data for subsequent analysis and classification; analyzing the data for expression of biomarkers of interest; and classifying data into classifications of distinct treatment parameter sets. The system can determine and classify the treatment parameters in which the there is a well regulated wound healing response. In a specific implementation, sirtuin expression levels are monitored over time after treatment to measure for an upregulation in sirtuin expression. The system determines distinct treatment parameters and sets of parameters that can upregulate the expression of the sirtuin family of genes, while not increasing the production of collagen. In other implementations, the system can determine and classify the treatment parameters that can increase collagen production, independently of or in addition to the upregulation of sirtuin. Based on the collected data, the system can also determine what treatment best optimizes the treatment parameters for patients on an individual basis. The classifications can be compiled in an index that can be applied to patients to select targeted and effective treatment.

The system allows determining a treatment regimen for a patient based on the patient's baseline levels of a gene, gene product, or other marker. The system includes: obtaining a sample from a patient and determining a baseline level from the sample; determining the treatment parameters based on the baseline level including using a classification system of predetermined baseline levels; and applying the selected treatment to the patient. In a specific implementation, a baseline sirtuin expression profile is obtained, and can be compared against a classification system (e.g., an index) of baseline sirtuin levels corresponding to various treatments and treatment parameters. If the patient's baseline level matches a level in the index, the parameters corresponding to the level are selected as the treatment. In a specific implementation, the parameters correspond to an EMR-based device treatment which upregulates the expression of the sirtuin family of genes, and does not increase collagen production. The classification reflects treatment regimens and parameters that can provide patients with customized and effective results.

The system can automate the selection of treatments for patients seeking medical and cosmetic procedures with a high likelihood of successful treatment. The system can rapidly, and at low cost, link patients to skin treatments approved and monitored by their physicians. This can eliminate the time and money that may be wasted on selecting and trying treatments that may not provide a patient with effective results.

Other objects, features, and advantages of the invention will become apparent upon consideration of the following detailed description and the accompanying drawings, in which like reference designations represent like features throughout the figures.

DETAILED DESCRIPTION OF THE INVENTION

Figure 1:
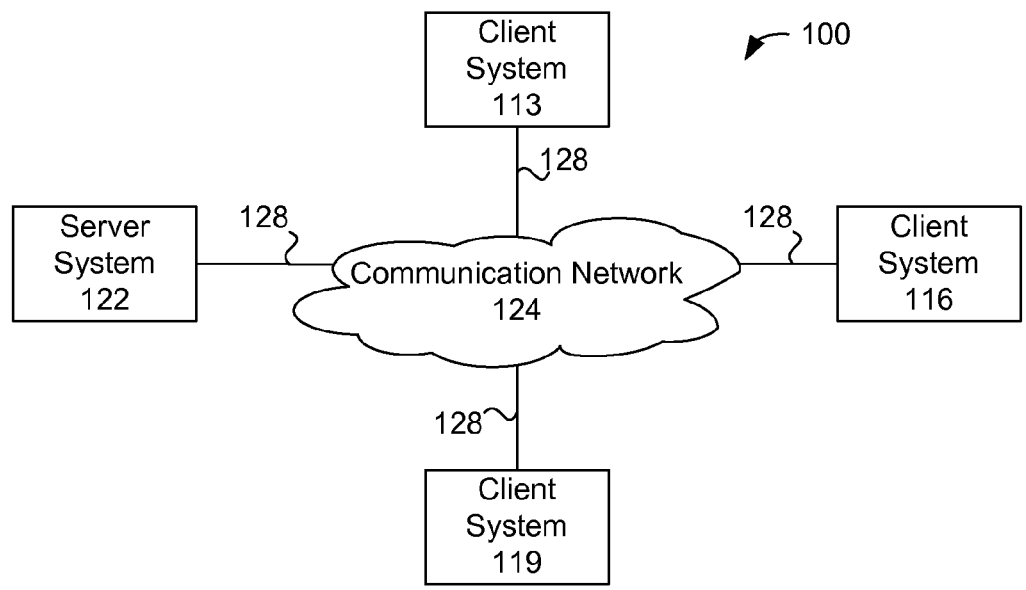
FIG. 1 shows a simplified block diagram of a distributed computer network within which a system of the invention can be implemented.

Skin aging results from a combination of extrinsic factors (e.g. chemical, toxins, pollutants, ultraviolet light, and ionizing radiation) and intrinsic factors (e.g. gene mutations, cellular metabolism, hormone environment). These factors manifest clinically as wrinkles, uneven pigmentation and loss of firmness. Histologically, epidermal and dermal atrophy are observed.

UV damage accelerates epidermal stem cell senescence and decreases the number and synthetic capacity of fibroblasts, the dermal cell responsible for production of extracellular matrix components. UV damage also reduces the synthetic capacity of fibroblasts by upregulating AP-1, which blocks transforming growth factor-β-mediated collagen gene transcription. Thus, the harmful effects of UV radiation have led to the development of a wide array of treatments aimed at reversing photodamage. These include topical retinoids, chemical peels, microdermabrasion, and the use of noninvasive EMR devices (e.g. lasers, light emitting diodes, intense pulsed light, and ultrasound). The efficacy of a novel, minimally invasive, microneedle-based bipolar FRF system for treatment of facial skin laxity and rhytides has also been investigated. The mechanisms underlying this reversal are thought to involve initiation of dermal remodeling leading to removal of photoaged dermal tissue and its replacement with new collagen and elastin.

However, studies have indicated that there is not always a direct correlation between collagen denaturation and collagen levels and the extent of clinical improvement in skin quality. Furthermore, recent clinical data also showed that FRF treatment too resulted in overall skin textural improvement, suggesting that dermal FRF treatment also induced anti-aging effects on the epidermal layer.

Research has led to the need to seek novel biomarkers that better correlate with clinical outcomes post-treatment with EMR-based devices and other non-EMR therapies. One potential target is sirtuins, a novel family of genes thought to regulate life span and improve stress resistance by controlling key cellular metabolic and signaling pathways. Although long term global reduced sirtuin expression has been shown to accelerate skin aging, its short term potential role in mediating the local anti-aging effects during wound healing after EMR-based device treatments remains largely unexplored.

The wound healing response has been established to follow a pattern of an initially strong inflammatory response and degradation of collagen followed by a gradual decrease in inflammation, apoptosis of immune cells, and collagen deposition. Sirtuins are a family of $NAD^+$ dependent protein deacetylases that has been implicated in anti aging and genetic stability pathways with specific links to genes and proteins such as Bax, Fork-head transcription factors, p53, and NF-κB, all of which are involved in the wound healing response.

FRF treatment can affect sirtuin anti-senescence pathways in skin. In particular, sirtuin activity may be an additional quantitative corollary for treatment efficacy.

Collagen denaturation, deposition and production are natural aspects of clinical improvement in skin quality, but are insufficient as sole and direct corollaries for effective treatment. Indeed, denaturation and deposition are steps involved in an overall comprehensive wound healing response, but alone are independent of aspects such as inflammation, proliferation or apoptosis of immune cells, and fibroblast longevity. Accordingly, a patient with a sustained reaction resulting in elevated levels of metalloproteinases (MMPs) and fibroblast genomic instability may not see clinical improvement in skin quality, even with positive indications from looking solely at the collagen levels.

On the other hand, establishing the sirtuin thresholds corresponding to a well regulated wound healing response may better correlate with improvements in skin quality, since sirtuin levels are intimately linked to not only collagen deposition and denaturation, but also to the immune response and fibroblast longevity. Therefore, there is a need to determine the treatment parameters for skin treatments, including EMR-based device treatment, chemical treatment, micordermabrasion, and others, that can upregulate the expression of sirtuin, without increasing collagen production.

FIG. 1 shows a simplified block diagram of a distributed computer network 100 in which a system of the present invention can be implemented. Computer network 100 includes a number of client systems 113, 116, and 119, and a server system 122 coupled to a communication network 124 via a number of communication links 128. Communication network 124 provides a mechanism for allowing the various components of distributed network 100 to communicate and exchange information with each other.

Communication network 124 may itself be comprised of many interconnected computer systems and communication links. Communication links 128 may be hardwire links, optical links, satellite or other wireless communications links, wave propagation links, or any other mechanisms for communication of information. Various communication protocols may be used to facilitate communication between the various systems shown in FIG. 1. These communication protocols may include TCP/IP, HTTP protocols, wireless application protocol (WAP), vendor-specific protocols, customized protocols, and others. While in one embodiment, communication network 124 is the Internet, in other embodiments, communication network 124 may be any suitable communication network including a local area network (LAN), a wide area network (WAN), a wireless network, a intranet, a private network, a public network, a switched network, and combinations of these, and the like. Distributed computer network 100 in FIG. 1 is merely illustrative of an embodiment incorporating the present invention and does not limit the scope of the invention as recited in the claims. One of ordinary skill in the art would recognize other variations, modifications, and alternatives. For example, more than one server system 122 may be connected to communication network 124. As another example, a number of client systems 113, 116, and 119 may be coupled to communication network 124 via an access provider (not shown) or via some other server system.

Client systems 113, 116, and 119 typically request information from a server computer system which provides the information. For this reason, servers typically have more computing and storage capacity than client systems. However, a particular computer system may act as both as a client or a server depending on whether the computer system is requesting or providing information. Additionally, although the invention has been described using a client-server environment, it should be apparent that the invention may also be embodied in a stand-alone computer system.

Server 122 is responsible for receiving information requests from client systems 113, 116, and 119, performing processing required to satisfy the requests, and for forwarding the results corresponding to the requests back to the requesting client system. The processing required to satisfy the request may be performed by server 122 or may alternatively be delegated to other servers connected to communication network 124.

Client systems 113, 116, and 119 enable users to access and query information stored by server system 122. In a specific embodiment, a "web browser" application executing on a client system enables users to select, access, retrieve, or query information stored by server system 122. Examples of web browsers include the Internet Explorer browser by Microsoft Corporation, the Firefox® browser by Mozilla Foundation, Chrome by Google Inc., WebKit and its variants, or others.

Figure 2:
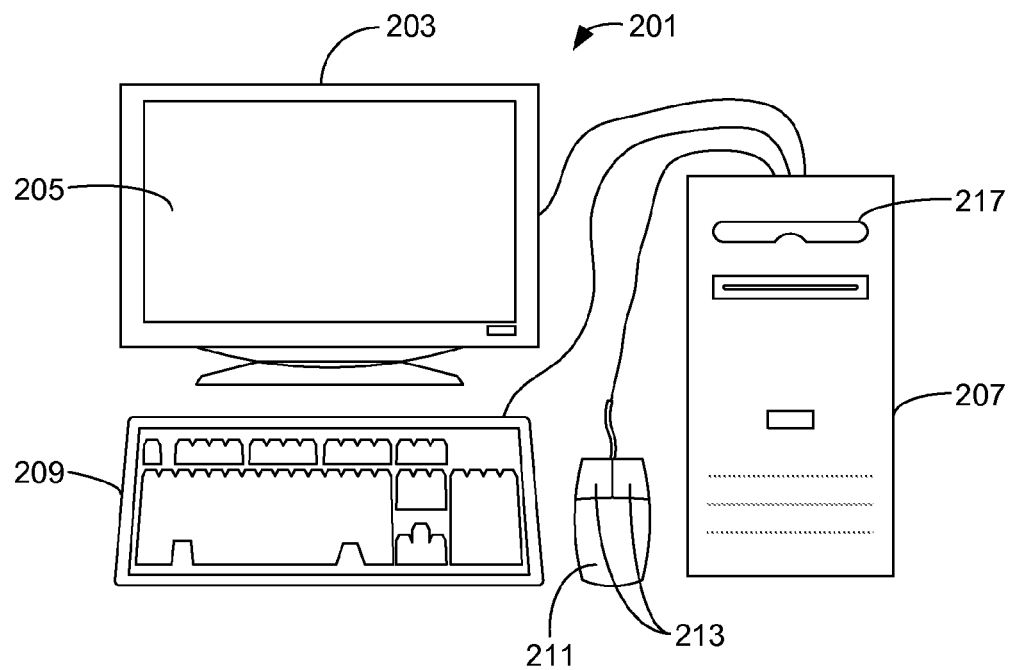
FIG. 2 shows a more detailed diagram of a computer system, client or server, which is used to operate with the system.

FIG. 2 shows a more detailed diagram of a computer system which may be a client or server. FIG. 2 shows a computer system 201 that includes a monitor 203, screen 205, cabinet 207, keyboard 209, and mouse 211. Mouse 211 may have one or more buttons such as mouse buttons 213. Cabinet 207 houses familiar computer components, some of which are not shown, such as a processor, memory, mass storage devices 217, and the like. Mass storage devices 217 may include mass disk drives, floppy disks, Iomega ZIP™ disks, USB removable storage, magnetic disks, fixed disks, hard disks, hard drives including both magnetic and flash storage in a single drive unit, CD-ROMs, recordable CDs, DVDs, DVD-R, DVD-RW, HD-DVD, Blu-ray DVD, flash and other nonvolatile solid-state storage, tape storage, reader, and other similar media, and combinations of these.

A computer-implemented or computer-executable version of the invention may be embodied using, stored on, or associated with computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on mass storage device 217. The source code of the software of the present invention may also be stored or reside on mass storage device 217 (e.g., hard disk, magnetic disk, tape, or CD-ROM). As a further example, code of the invention may be transmitted via wires, radio waves, or through a network such as the Internet.

The computer system in FIG. 2 is representative of electronic computing systems with a computer processor or central processing unit (CPU). These include servers, desktop computers, workstations, notebook or laptop computers, tablets, nettops, netbooks, smartphones, set-top boxes, media players, and many others. These can also include iPads, iPhones, PDAs, or Android phones.

Figure 3:
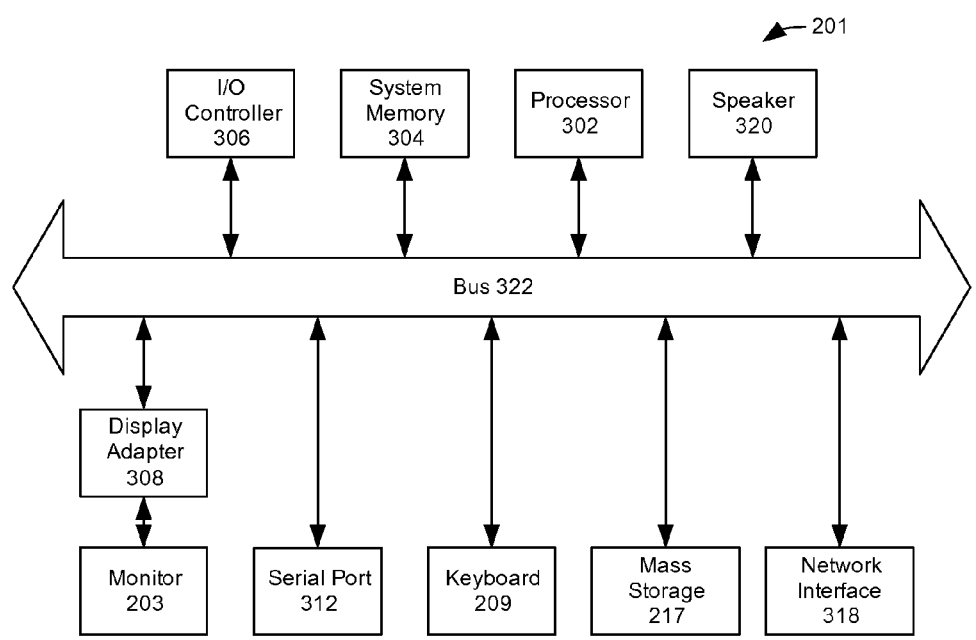
FIG. 3 shows a system block diagram of a computer system used to execute a software implementation of the invention.

FIG. 3 shows a system block diagram of computer system 201 used to execute software. As in FIG. 2, computer system 201 includes monitor 203, keyboard 209, and mass storage devices 217. Computer system 201 further includes subsystems such as central processor 302, system memory 304, input/output (I/O) controller 306, display adapter 308, serial or universal serial bus (USB) port 312, network interface 318, and speaker 320. The invention may also be used with computer systems with additional or fewer subsystems. For example, a computer system could include more than one processor 302 (i.e., a multiprocessor system) or a system may include a cache memory. The processor may be a multicore processor, such as the Intel Core 2 Duo, Intel Pentium® D, AMD Athlon™ 64 X2 Dual-Core, AMD Phenom™, Microsoft Xbox 360 central processing unit (CPU), and ARM architecture based processors (e.g., Nvida Tegra 2, Nvida Tegra 3, Qualcomm Snapdragon, Apple A4, Apple A5, Apple A5X, or Apple A6).

Further, the system can include a camera, web cam, video camera, or other image capture device. The image capture device can be integrated or can be a standalone camera (or scanner) that can be connected to the system via a cable (e.g., USB) or wirelessly (e.g., NFC, Bluetooth, or W-Fi). The system can include a microphone or other audio input device. The audio input device can be an external microphone that is connected to the system via a cable (e.g., USB) or wirelessly (e.g., NFC, Bluetooth, or Wi-Fi).

Arrows such as 322 represent the system bus architecture of computer system 201. However, these arrows are illustrative of any interconnection scheme serving to link the subsystems. For example, speaker 320 could be connected to the other subsystems through a port or have an internal direct connection to central processor 302. Computer system 201 shown in FIG. 2 is but an example of a computer system suitable for use with the present invention. Other configurations of subsystems suitable for use with the present invention will be readily apparent to one of ordinary skill in the art.

Computer software products may be written in any of various suitable programming languages, such as C, C++, C#, Pascal, Fortran, Perl, Matlab (from MathWorks, www.mathworks.com), SAS, SPSS, JavaScript, AJAX, Java, Erlang, and Ruby on Rails. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows Vista, Windows 7, Windows 8, Windows CE), Linux, UNIX, Sun OS, Ubuntu, or Macintosh OS X. Microsoft Windows is a trademark of Microsoft Corporation. Some mobile operating systems that can be used with an implementation of the invention include: Google Android, Chrome OS; Apple iOS4 or iOS5; Blackberry OS; Windows Phone.

Furthermore, the computer may be connected to a network and may interface to other computers using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, 802.11n, 802.11 ac, and 802.11 ad, just to name a few examples), near field communication (NFC), radiofrequency identification (RFID), mobile or cellular wireless (e.g., 2G, 3G, 4G, 3GPP LTE, WiMAX, LTE, LTE Advanced, Flash-OFDM, HIPERMAN, iBurst, EDGE Evolution, UMTS, UMTS-TDD, 1xRDD, and EV-DO). For example, signals from a computer may be transferred, at least in part, wirelessly to components or other computers.

Figure 4:
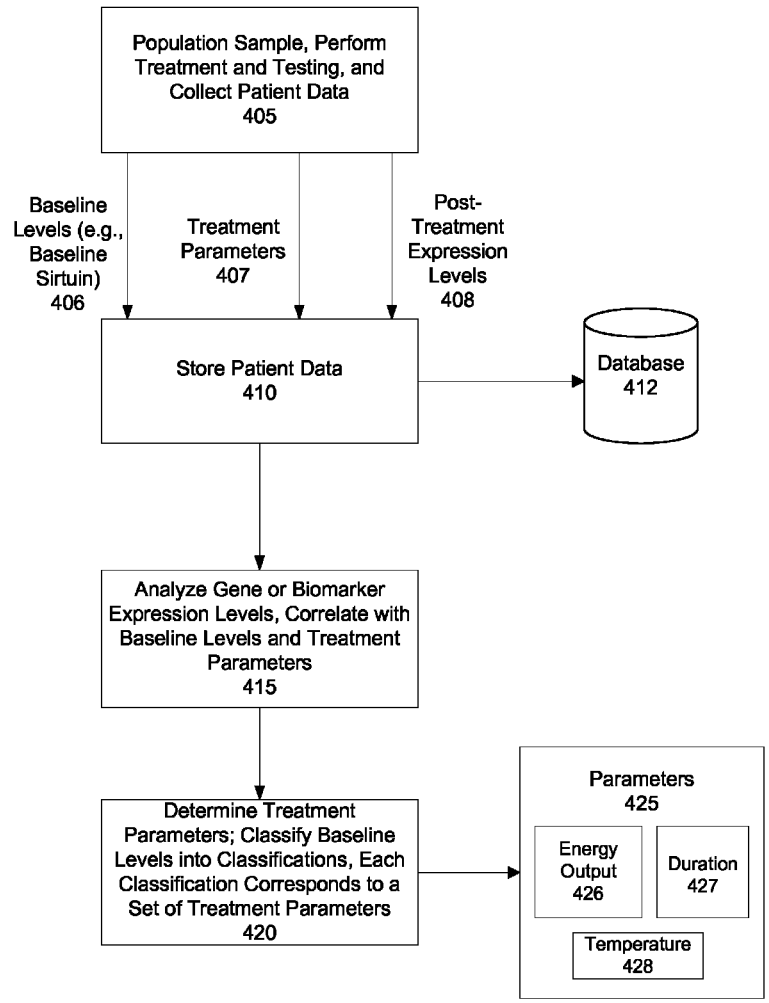
FIG. 4 shows a system of evaluating skin treatment.

FIG. 4 shows a system of evaluating a skin treatment and determining treatment parameters. In the specific implementation of FIG. 4, the system uses sirtuin expression as a biomarker for determining treatment parameters as well as for evaluating the efficacy of skin treatments across populations of patients. The system can track sirtuin expression levels and establish the necessary levels to result in a clinical improvement and can allow for a standardization of sirtuin thresholds. The system determines the parameters for EMR based device treatments that cause an upregulation in the expression of sirtuin genes. The system is not limited to noninvasive EMR treatment devices that use FRF systems, lasers, light emitting diodes, intense pulsed light (IPL), microwave, infrared, ultrasound, and others. For example, the system can be applied to other methods, such as ablative CO2 laser treatment, IPL, and others, to both calibrate and evaluate an effective treatment, by determining which modality and treatment regimen best establishes the sirtuin thresholds determined to result in a clinical improvement.

Clinically, this calibration may lead to a higher percentage of successful cosmetic treatments. Therefore, further investigation into the sirtuin response to skin treatments may allow for the calibration of current and development of new devices that can be finely tuned based on sirtuin thresholds to ensure a well regulated wound healing response, increasing the likelihood of successful skin treatment.

The system has components to generate biological data from a population sample of subjects. The data can be used to determine distinct treatment parameters and to classify treatments that will be effective for patients in promoting a well regulated wound healing response and clinical outcome. Components include: selecting a population sample, performing treatment and testing, and collecting patient data for this sample 405. The collected data can include measurements such as a patient's baseline sirtuin level 406 prior to a treatment, and the patient's sirtuin expression levels 408 after the treatment. The treatment parameters 407 are also collected. This data can be stored 410 in, for example, a database 412, for subsequent analysis and classification 415. This analysis determines the treatment parameter sets in which the there is a well regulated wound healing response. In a specific implementation, sirtuin expression levels are monitored over time after treatment to measure for an upregulation in sirtuin expression. These treatments and treatment data can be classified based on patients' baseline levels of biological markers 420. In a specific implementation, patient's baseline sirtuin gene expression profile is used. Other data and markers that can be used in addition to or in combination with sirtuin level include collagen, elastin, metalloproteinases, and extracellular matrix markers on a gene chip and skin test at baseline. This would be a more comprehensive biomarker profile for anti-aging applications that would then correspond to which choice of EMR or chemical treatment(s) is best for each treatment. Based on the collected data, the system can determine what treatment best optimizes the treatment parameters for patients. The classifications can be compiled in an index that can be applied to patients to select targeted and effective treatment.

The system in FIG. 4 can determine the treatment parameters and achieve classifications of treatment for a general population or for a targeted population. For example, target populations can be based on geography, ethnicity, biological features, or other parameters, or combinations of these. The system can be tailored to specific populations. This will ensure the system can be effectively applied to the great majority of the patients in those populations.

The actual population size of an entire population can be enormously large. It is impractical to make measurements of every individual in the population. So instead, a sample of the population is taken to reduce a number of measurements needed. Accurate results are desirable so the population sample should be sufficiently large to give good results which represent the entire population.

Performing treatment, testing and collection of data can include on-site patient treatment and monitoring at doctors offices, hospitals, clinics, testing centers and laboratories, or at-home treatment. The patient baseline levels can be collected prior to an administered treatment. This can include gathering a biological sample including a skin or tissue biopsy, a blood test, a skin test, or any combination of these. In a specific implementation, a sample is obtained from a patient to determine the patient's sirtuin gene expression profile. In other implementations, a tissue sample or a skin test can be used to determine a patient's collagen, elastin, metalloproteinases, and extracellular matrix markers on a gene chip at baseline. This testing can be performed independently or in combination with sirtuin level testing.

The treatment can include noninvasive EMR treatment devices (e.g., FRF systems, lasers, light emitting diodes, intense pulsed light, microwave, infrared, ultrasound, and others), and other methods (e.g., ablative CO2, IPL, chemical treatments, microdermabrasion and others). In a specific implementation, fractional radiofrequency devices and methods are used to generate radiofrequency (RF) thermal zones to the reticular dermis, while sparing the epidermis and adnexa. In a specific implementation, Renesis™, a minimally invasive radiofrequency device developed by Primaeva Medical, Inc., was used to treat patients. All trademarks or registered trademarks in this application are the property of their respective owners.

In a specific implementation, the treatment method and parameters are as follows. Preceding each treatment, skin was cleansed using 70 percent isopropyl alcohol, followed by wiping with topical 10 percent povidone iodine antiseptic. Subjects were then infiltrated with 1 to 2 percent lidocaine with or without 1:100,000 epinephrine (or adrenaline). The FRF system was used to deliver bipolar RF energy to the dermis via 5 microneedle 30 gauge electrode pairs 6 millimeters in length, each spaced 1.25 millimeters apart. The angle of microneedle skin insertion was about 20 degrees. During RF energy application, the dermal tissue temperature within the treatment target zone was maintained at 72 degrees Celsius for 4 seconds using an intelligent feedback system. Superficial cooling to minimize epidermal damage was achieved using a solid state Peltier device equipped with a heat sink and fan maintained at 15 degrees Celsius.

Collection of biological data from patients include collection of tissue samples from the treated area on the patients' bodies. In a specific implementation, patient samples were taken and tested immediately, at 2 days, 14 days and 28 days after the treatment in order to capture the temporal evolution of the in vivo wound healing response. Tissue can be sampled at other times including at 1, 3, 4, 5, 6, 7, 8, 9, 10, 11, 12, 13, 15, 16, 17, 18, 19, 20, 21, 25, 30, 35, 40, 45, 50 days, or greater, or any combination of these, post treatment. In general, more samples analyzed can provide more accurate measurement of the progression of the gene expression.

Standard DNA analysis tests can be performed to isolate genes of interest, including a semi-quantitative reverse transcriptase-polymerase chain reaction (RT-PCR) analysis. Any isolation and amplification methods known in the art can be used.

Gene of interest expression changes can be compared against a temporally stable internal control, such that any variation in gene expression post-normalization would likely be due to the FRF treatment rather than variations between samples. In a specific implementation, GAPDH and β-actin were both considered for this control.

Collection of data further includes recording the treatment parameters of the treatment procedure administered. These can include the type of treatment, the device settings, energy level of the device setting (e.g., electrical energy, light energy, or a combination of these), pulse duration, temperature of the heat applied to the tissue, total time of application, cooling system parameters, frequency of the treatment, and others. For example, in FRF treatments, the dermal tissue temperature within the treatment target zone can be maintained in a range from about 55 degrees Celsius to about 85 degrees Celsius (e.g., 60, 60.5, 61, 61.5, 62, 63, 64, 65, 66, 67, 68, 68.5, 69, 69.5, 70, 70.5, 71, 71.5, 72, 73, 74, 75, 76, 77, 78, 79, 80, 81, 82, 83, or 84 degrees) for a duration in a range from about 1 second to about 30 seconds (e.g., 1, 2, 3, 4, 5, 6, 7, 8, 9, 10, 12, 15, 20, 22, 25, 27, 29, or more seconds). The energy output can vary depending on the application.

These raw data can be stored in a database. The database can be read, accessed, analyzed, and processed by a computer system, which is hardware and software for processing and storing data. Some examples of computer system hardware include computer processors (e.g., multicore processors), computer-readable medium, memory or nonvolatile memory on which the measurement data and software programs are stored. The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

To analyze the parameters and generate the classifications index, the components or subcomponents of the analysis and classification component can include and be performed by a computer system. The computer system can include, for example, a computer screen to electronically display graphs and charts. The computer system can include software programs stored in computer memory for performing (via a computer processor) the statistical analyses.

Various methods can be used to analyze the collected data. These can include baseline sirtuin level charts, sirtuin gene expression charts, collagen production charts (e.g., indicating the level of collagen production in the tissue post treatment), distribution graphs, comparative distribution graphs (e.g., comparing different populations). The analysis can include statistical analyses and calculations of the data. A distribution curve graph may be displayed on a screen of a computer system, printed on paper using a printer, or both. The data can be represented using other types of graphs such as a histogram or pie chart. A histogram is a representation of a frequency distribution using rectangles whose widths represent class intervals and whose areas are proportional to the corresponding frequencies.

Chart data, graph data, or a combination of these can be analyzed to determine parameters 425 that induce an upregulation of a particular biomarker (e.g., sirtuin expression levels). For example, a healthy wound healing response resulting from a specific treatment regimen, along with the corresponding treatment parameters applied, includes increased sirtuin expression levels of about 50 to 100 percent post treatment, while collagen production levels are not induced. However, in other implementations, the system can analyze the data to determine those distinct treatment parameters that can induce both sirtuin expression and collagen production post treatment.

In a specific implementation, treatment parameters for various EMR devices that can lead to upregulation of the sirtuins is classified. Independent of or in combination with this classification, treatment parameters for EMR devices that can increase collagen production is also classified. For example, certain categories of treatments and parameters can increase the sirtuin gene expression post treatment, while other categories can promote collagen production. And certain categories of treatments and parameters settings can increase both sirtuin expression and collagen production. For example, a category can indicate a specific range of energy level settings for a FRF treatment system that can induce upregulation of sirtuin expression without collagen increases. This can be helpful since optimizing collagen production may not the best way to achieve anti aging effects, while increases of sirtuin expression can better correlate with clinical efficacy. Induced sirtuin expression can be a primary factor in producing anti aging benefits while collagen production is a secondary factor.

The data can be partitioned to generate classifications of treatments according to patient's baseline levels. For example, a patient with a specific baseline sirtuin expression profile can fall into one or more categories of treatments with specific sets of treatment parameters that are provide the best treatment outcome for that patient on an individual basis. Other biomarkers including collagen, elastin, metalloproteinases, and extracellular matrix markers can be analyzed to determine what treatment best optimizes the treatment parameters. This can provide patients with effective treatments based on their biological makeup and at low costs.

The classification can include an index of baseline levels. For example, baseline sirtuin levels can be indexed or arranged in an order. Each level, or a range of levels, can correspond to a set of treatment parameters that will yield effective treatment results for a patient having that specific baseline sirtuin level. One level can correspond to a single treatment having a specific set of parameters, more than one set of parameters, or one of more types of treatment (e.g., FRF and light therapy) having different sets of parameters. The parameters can be altered depending on the specific gene, gene product, or component to be regulated during the wound healing response.

The set of treatment parameters 425 for input into a skin treatment device can cause upregulation of expression of the sirtuin family of genes in the tissue after treatment is administered. In a specific implementation, the parameter set includes an energy level output 426 of the device (e.g., electrical energy, light energy, or a combination of these), a total time of application 427, and a temperature 428 of the heat applied to the tissue. It should be understood that the invention is not limited to the specific parameters presented. A parameter set of the invention may have additional parameters (not necessarily described in this application), different parameters which replace some of the parameters presented, fewer of the parameters presented, or any combination of these. Further, the parameters in other implementations of the invention may not be exactly the same as those presented and may be modified or altered as appropriate for a particular application or based on the data or situation. For example, other parameters can include cooling system parameters, frequency of the treatment, duration of pulse, and others. The parameter set can be used in other skin treatments including all EMR-based device treatments, chemical treatments, microdermabrasion treatments, and other skin treatments. Entry of the parameter set into these other treatment devices can also cause an upregulation of biomarkers such as the sirtuin gene, increase in collagen production, or both.

Figure 5:
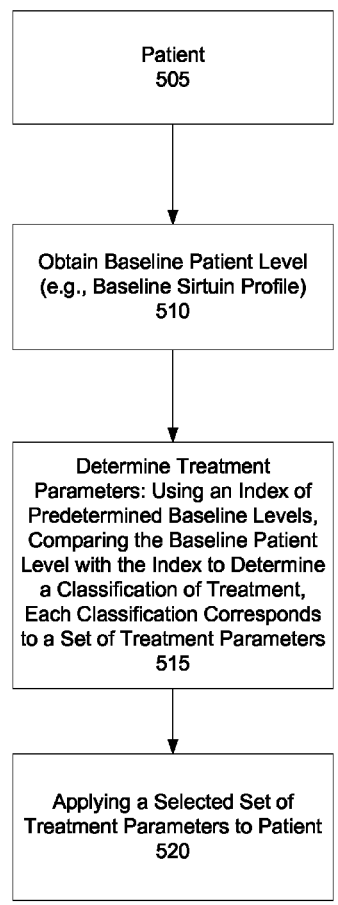
FIG. 5 shows a flow diagram for determining a skin treatment for a patient.

FIG. 5 shows a flow for determining a skin treatment and treatment parameters for a patient 505 based on the patient's baseline levels. The system components can assess a patient's genetic profile, skin profile, other biological factors, or a combination of these to select a treatment regimen or regimens that will provide effective treatment outcomes. Components include: obtaining a baseline level from a patient 510. In a specific implementation, a baseline sirtuin expression profile is obtained. Methods of gathering a biological sample including a skin or tissue biopsy, a blood test, a skin test, or any combination of these can be used. Determining a treatment can include using a classification system of predetermined baseline levels 515. For example, an index of baseline sirtuin levels corresponding to various treatments and treatment parameters can be used. The patient's baseline level is compared against the index to determine the classification of treatment for the patient. The classification reflects a particular treatment regimen with distinct parameters that can provide the patient with effective results. The selected treatment is applied to the patient 520.

Performing testing and collection of patient data can include on-site patient testing at doctors offices, hospitals, clinics, testing centers and laboratories, or at-home testing (e.g., home use kits). The patient baseline levels can be collected prior to an administered treatment. This can include gathering a biological sample including a skin or tissue biopsy, a blood test, a skin test, or any combination of these. In a specific implementation, a tissue sample is obtained from a patient to determine the patient's sirtuin gene expression profile. In other implementations, a tissue sample or a skin test can be used to determine a patient's collagen, elastin, metalloproteinases, and extracellular matrix markers on a gene chip at baseline levels. This testing can be performed independently or in combination with sirtuin level testing.

Standard DNA analysis tests can be performed to isolate genes of interest, including a semi-quantitative RT-PCR analysis. Any isolation and amplification methods known in the art can be used.

Determining a skin treatment can include comparing a patient's baseline levels with a predetermined index or list of baseline levels for a general population or for a target population. To compare and classify the patient data, the components or subcomponents can include and can be performed by a computer system. The computer system can include, for example, a computer screen to electronically display tables, charts, an index, and results. The computer system can include software programs stored in computer memory for performing (via a computer processor) the analyses.

The system can include a software application. The application can be a standalone program such as a desktop application, operating on a desktop or laptop computer, or a mobile smartphone or tablet application. In another embodiment, the application is a network- (or cloud-) based application that is stored at a server. A user (e.g., doctor, nurse, or laboratory technician) accesses the application through a web browser application (e.g., Internet Explorer, Chrome, Safari, and Firefox). The user can submit, select, access, retrieve or query information stored by the server system via a network.

For example, using the software's user interface, a doctor can input the patient's baseline level index. The baseline level can be transmitted from the user device over the network (such as the Internet) to a server. The connection between server and user device may be a secure connection (such as being encrypted, or protected using a SSL certificate). The server also includes software, such as diagnostic software, treatment software, and other software to process the information received from the client device. The server software can classify the patient's baseline level and transmit specific treatments and parameters to the user device via the network.

The software is one component of a system that allows rapid, automated classification of a patient's baseline profile to determine an effective treatment on an individual basis. Individual patients benefit by having a customized treatment regimen prescribed and at an overall lower cost than is currently possible.

The system can match the patient's baseline levels with the predetermined levels in the classification to select a treatment regimen and parameters. Each category or classification of treatment corresponds to a set of treatment parameters that can maximize the patient's wound healing response post treatment. A healthy wound healing response involves the restoration of cell populations in the treated area to normal levels through the apoptosis of recruited inflammatory immune cells, and an inhibition of inflammation to prevent a runaway inflammatory response.

In a specific implementation, the system determines the treatment parameters that upregulates sirtuin expression, which promotes these wound healing effects. The system can also determine treatments that induce production of collagen and the protection of collagen producing fibroblasts. This analysis can be performed independently of or in combination with the sirtuin level analysis. For example, the system can determine the skin treatment that will induce sirtuin expression post treatment, without inducing collagen production. This can be helpful since collagen production may not be sufficient as a sole and direct corollary for effective treatment. In other implementations however, the system can determine the treatments and parameter settings that will induce both sirtuin expression and collagen production.

Figure 6:
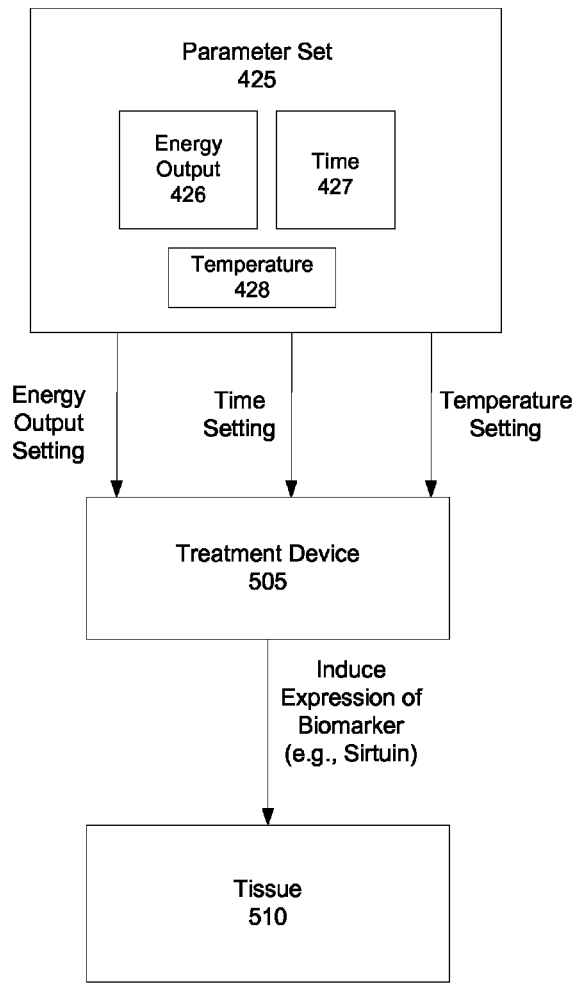
FIG. 6 shows a system of inducing expression of a biomarker caused a treatment parameter set.

FIG. 6 shows a system of inducing expression of a biomarker caused by a set of treatment parameters entered into a device of a skin treatment. A first set of treatment parameters 425 for a skin treatment device 505 causes upregulation of expression of the sirtuin family of genes in the tissue 510 after a treatment is administered. The parameter set includes an energy level output 426 of the device (e.g., electrical energy, light energy, or a combination of these), a total time of application 427, and a temperature 428 of the heat applied to the tissue. The parameters are input into the skin treatment device before applying the treatment to a patient. It should be understood that the invention is not limited to the specific parameters presented. A parameter set of the invention may have additional parameters (not necessarily described in this application), different parameters which replace some of the parameters presented, fewer of the parameters presented, or any combination of these. Further, the parameters in other implementations of the invention may not be exactly the same as those presented and may be modified or altered as appropriate for a particular application or based on the data or situation. For example, other parameters can include cooling system parameters, frequency of the treatment, duration of pulse, and others.

A second set of treatment parameters for the treatment device causes increase in collagen production in the tissue after treatment. The second set of parameters can be different from, identical to, or include components of the first set of parameters. A third set of treatment parameters for the skin treatment device causes upregulation of sirtuin expression and an increase in collagen production in the tissue post treatment. The third set of parameters can be different from, identical to, or include components of the first set of parameters or the second set of parameters. In implementations, the set of parameters includes an energy output of the device, a duration of the treatment, and a temperature setting for the tissue. The treatment parameters can be used in EMR-based treatments, chemical treatments (e.g., chemical peels), microdermabrasion treatments, and other skin treatments to cause upregulation in the expression of biomarkers in the tissue.

In a specific implementation, the treatment is a FRF device treatment, and the dermal tissue temperature within the treatment target zone can be maintained in a range from about 55 degrees Celsius to about 85 degrees Celsius (e.g., 60, 60.5, 61, 61.5, 62, 63, 64, 65, 66, 67, 68, 68.5, 69, 69.5, 70, 70.5, 71, 71.5, 72, 73, 74, 75, 76, 77, 78, 79, 80, 81, 82, 83, or 84 degrees) for a duration in a range from about 1 second to about 10 seconds (e.g., 1, 2, 3, 4, 5, 6, 7, 8, 9, or 10 seconds). The energy output can vary depending on the application. The parameter set can cause an upregulation of sirtuin expression in the tissue without inducing collagen production.

A method for inducing expression of a biomarker in tissue after a treatment is applied to the tissue includes inputting a first set of parameters, as described above, into a treatment device. In a specific implementation, the biomarker is a sirtuin gene where the sirtuin gene expression is increased by the set of parameters. In another specific implementation, the biomarker is a collagen deposition and production value, where the collagen production is increased by the set of parameters. In yet another specific implementation, the set of parameters can cause both an increase in the expression of sirtuin and production of collagen in the tissue. The treatment parameters are input into a device of a EMR-based treatments, chemical treatments (e.g., chemical peels), microdermabrasion treatments, and other skin treatments to cause upregulation in the expression of biomarkers in the tissue.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method comprising:
measuring data from a group of patients, wherein the data comprises a first expression level before a skin treatment for a patient's skin and a second expression level after the treatment, wherein the treatment corresponds to a first set of treatment parameters, the first expression level comprises a first sirtuin gene expression and the second expression level comprises a second sirtuin gene expression;
using a processor, determining a first difference between the second expression level and the first expression level, and establishing a first threshold value for the first difference corresponding to the first and second sirtuin gene expression based on the data, and
if the second expression level exceeds the first expression level for the sirtuin gene expression by at least the first threshold, selecting the first set of treatment parameters for the patient's skin; and
treating the patient's skin according to the selected first set of treatment parameters.

2. The method of claim 1 wherein the first expression level comprises a sirtuin gene expression.

3. The method of claim 1 wherein the second gene expression level comprises a sirtuin gene expression.

4. The method of claim 1 wherein the first expression level comprises a first collagen production value and the second expression level comprises a second collagen production value, and the first set of treatment parameters selected does not result in the second collagen production value being higher than the first collagen production value.

5. The method of claim 1 wherein the skin treatment comprises an electromagnetic radiation based device treatment.

6. The method of claim 5 wherein the electromagnetic radiation based device treatment comprises a fractional radiofrequency treatment.

7. The method of claim 1 wherein the skin treatment comprises a chemical based skin treatment.

8. The method of claim 1 comprising:
measuring data from the group of patients, wherein the data comprises a third expression level before the treatment and a fourth expression level after the treatment;
using a processor, determining a second difference between the fourth expression level and the third expression level, and
if the second difference exceeds a second threshold, selecting a second set of treatment parameters.

9. The method of claim 8 wherein the first and second expression levels comprise a sirtuin gene expression, the third and fourth expression levels comprise a collagen production value, and
the second set of treatment parameters is different from the first set of treatment parameters.

10. The method of claim 8 wherein the first and second expression levels comprise a sirtuin gene expression, the third and fourth expression levels comprise a collagen production value, and
the first and second set of treatment parameters are the same.

11. The method of claim 1 wherein the first set of treatment parameters comprises an energy output value, a temperature setting of the treatment, and a total time of the treatment.

12. The method of claim 11 wherein the skin treatment comprises a fractional radiofrequency treatment.

13. A system comprising:
a processor that executes a method for skin treatment comprising:
determining a first patient baseline level, wherein the first patient baseline level comprises a sirtuin gene expression level;
determining an index for determining skin treatment parameters, wherein the index indicates a plurality of predetermined baseline levels, wherein each predetermined baseline level corresponds to a set of treatment parameters that can be applied to a patient's skin in order for the patient's skin to show an improvement;
determining a plurality of treatment parameters for treating skin of the first patient, wherein the treatment parameters are obtained from determining based on the index one of a plurality of predetermined baseline levels that corresponds to the first patient baseline level comprising the sirtuin gene expression level; and
treating the patient's skin according to the plurality of treatment parameters.

14. The system of claim 13 wherein the determining skin treatment parameters comprises:
determining if there is an entry for the first patient baseline level in the index of predetermined baseline levels;
if there is an entry for the first patient baseline level, selecting the predetermined baseline level and the corresponding set of treatment parameters; and
applying the treatment parameters to the patient.

15. A system comprising:
a processor that executes a method for skin treatment comprising:
determining a first patient baseline level, wherein the first patient baseline level comprises a collagen production value;
determining an index for determining skin treatment parameters, wherein the index indicates a plurality of predetermined baseline levels, wherein each predetermined baseline level corresponds to a set of treatment parameters that can be applied to a patient's skin in order for the patient's skin to show an improvement;
determining a plurality of treatment parameters for treating skin of the first patient, wherein the treatment parameters are obtained from determining based on the index one of a plurality of predetermined baseline levels that corresponds to the first patient baseline level comprising the collagen production value; and
treating the patient's skin according to the plurality of treatment parameters.

16. The system of claim 15 comprising a second patient baseline level, wherein the second patient baseline level comprises a marker other than the collagen production value; and
a plurality of treatment parameters for treating skin of the second patient, wherein the treatment parameters are obtained from determining based on the index one of a plurality of predetermined baseline levels that corresponds to the second patient baseline level.

17. The system of claim 15 comprising:
a second patient baseline level, wherein the second patient baseline level comprises a collagen production value; and
a plurality of treatment parameters for treating skin of the second patient, wherein the treatment parameters are obtained from determining based on the index one of a plurality of predetermined baseline levels that corresponds to the second patient baseline level comprising the collagen production value.

18. A method comprising:
taking a measurement of a patient, wherein the measurement comprises a first expression level of a first biomarker before a skin treatment for a patient's skin and a second expression level of the first biomarker after the treatment, wherein the treatment corresponds to a first set of treatment parameters;
using a processor, determining a first predetermined difference between the second expression level and the first expression level, and establishing a first threshold value for the first predetermined difference corresponding to the first and second expression level based on the data, and
if the second expression level exceeds the first expression level by at least the first predetermined threshold, selecting the first set of treatment parameters, and
treating the patient's skin according to the selected first set of treatment parameters.

19. The method of claim 18 wherein the applying the first set of treatment parameters to the patient comprises inputting the first set of treatment parameters into a treatment device.

* * * * *